April 19, 1927.

E. B. THOMAS

SANITARY NAPKIN OR THE LIKE

Re. 16,603

Original Filed March 13, 1925

Inventor:
Errold B. Thomas,
by Emery, Booth, Janney & Varney
Attys.

Reissued Apr. 19, 1927. Re. 16,603

UNITED STATES PATENT OFFICE.

ERROLD B. THOMAS, OF NEWTON, MASSACHUSETTS, ASSIGNOR TO THOMAS PRODUCTS, INC., OF BOSTON, MASSACHUSETTS, A CORPORATION OF MASSACHUSETTS.

SANITARY NAPKIN OR THE LIKE.

Original No. 1,564,498, dated December 8, 1925, Serial No. 15,241, filed March 13, 1925. Application for reissue filed February 17, 1927. Serial No. 169,113.

My invention relates to the manufacture of absorptive devices for hygienic and surgical purposes, and more particularly aims to provide an improved ligno-cellulose serviette, sanitary napkin or the like and method of making the same.

Certain ligno-cellulose materials now manufactured upon a commercial scale have been found to possess characteristics making them suitable for use in forming surgical dressings, absorbent pads and the like, particularly celluloses or so called "cellulose cotton" of the coniferous woods, including paper makers' cellulose pulp and like fibrous materials. Among said characteristics are the high absorptive efficiency of such wood cellulose, its lightness, its capability of being purified and, if desired, delivered in a sterile condition and its relative inexpensiveness as compared for example with that of "natural" cotton. One of the important advantages of such material from a practical viewpoint, perhaps the most important advantage particularly in its application to sanitary napkins, with which my invention is especially though not exclusively concerned, is its ability readily to disintegrate thus permitting the article easily to be disposed of after use, as through the usual toilet facilities without liability of causing stoppages in the plumbing systems.

On the other hand there have heretofore been certain objectionable features in sanitary napkins or serviettes formed of wood cellulose. Due to the extremely high absorptive properties of that material—approximately five times that required by the United States Government standard for hospital dressings—and to its extreme lightness and tenuous nature it is apt to become permeated too quickly by the liquid to be absorbed, with objectionable results. A further objection has been found in the tendency of the fibres to mat together at the edges of the pad, as during the cutting or stamping out thereof from a larger sheet or strip of the material, sometimes resulting, particularly in the less expensive grades of wood cellulose in relatively stiff or wiry formations which tend to cause irritation.

In accordance with my invention means is provided whereby said objections are wholly overcome while at the same time the general softness, flexibility and, most important, the ability of the pad to disintegrate rapidly and easily when discarded after use are in no wise impaired.

In the drawings showing by way of example one embodiment of my invention and illustrating one method of making the same:

Figure 2:
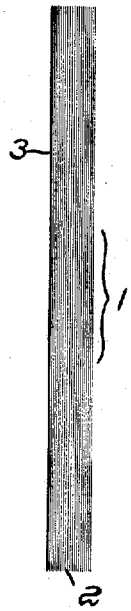
Fig. 2 is a side elevation of the absorptive element of Fig. 1.
Figure 3:
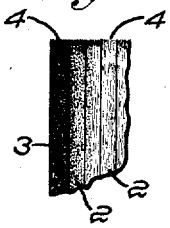
Fig. 3 is a detail upon a greatly enlarged scale of a portion of Fig. 2.

Referring now more particularly to the drawings, the absorptive element or pad 1, as best seen in Figs. 2 and 3, comprises a multiplicity of layers 2, 2, etc., each consisting of a film or thin sheet of the wood cellulose or other cellulosic material above referred to, any desired number of suitable layers or tenuous films being employed. Desirably at least thirty of the thinnest and most tenuous wood cellulose films practically manufacturable are superposed.

As above pointed out such a package or pad is highly absorptive, light, flexible and readily separable or capable of being disintegrated after use. It will, however, become too quickly penetrated from the inner to the outer side by the fluid to be absorbed. To overcome this defect I have devised means whereby one side or surface, that upon the outside when the napkin is applied to the body, is rendered moisture proof, so that the absorbed liquid is retained by the pad and prevented from penetrating through its outer surface, and this without detracting appreciably from the flexibility of the napkin, or its ability to be disintegrated.

Said moisture proof surface for the pad is indicated at 3 in Figs. 2 and 3. It will be noted that it constitutes but a very small fraction of the total thickness of the pad. Said surface 3 is, in accordance with my invention, so applied that the pad as a whole is not stiffened or rendered less flexible nor are the greater majority of the sheets or films 2, 2, etc. in any wise unified or inseparably connected. I obtain said results preferably by subjecting a sheet of wood cellulose or other cellulosic material similar to the film-like sheets 2 but of a closer texture, less tenuous and heavier to a bath of a special moisture proofing material. In practice said material may be a rubber or rubber-like compound or a high-melting paraffin or wax, said material being of high flexibility when dry, not stiff or harsh, and having a melting point well above body temperatures so as not to be rendered viscous or sticky thereby. Since an important object of my invention is to add substantially no stiffness to the pad and not to hinder it from disintegrating when desired and yet to provide a moisture proof surface many materials such as starch, cement-like material, low-melting glues and certain gum sizes and the like have been found wholly unsatisfactory.

In forming the absorbent pad embodying my invention and in accordance with the method thereof a multiplicity of film-like strips or webs of the wood cellulose are superposed or piled in any suitable manner, as by feeding from a roll. The moisture proofing surface is then applied. Since any moisture proofing material must not penetrate the pad to any substantial degree it is undesirable to apply said material either in a spray or other form directly to the superposed webs, the absorptive properties of the latter being so marked that any material suitable for the purpose and so applied will impregnate the webs or penetrate them so far as to make them stiff and not readily separable. Accordingly I preferably provide a sheet or web of wood cellulose or other cellulosic material of appreciably greater substance than said multiplicity of webs and conduct the same through a bath of the moisture proofing material such as above mentioned, drain it of any excess material, and then lay it desirably while still moist, upon the superposed webs. Said sheet is sufficiently substantial to retain practically all of said moisture proofing material, so that but one, or at the most a very small plurality of the underlying films, will be penetrated by the material, as indicated by the stippling in Fig. 3. Said waterproofed sheet will be lightly held in position by the material but preferably is entirely free of positive securing means such as stitches or the like.

Figure 1:
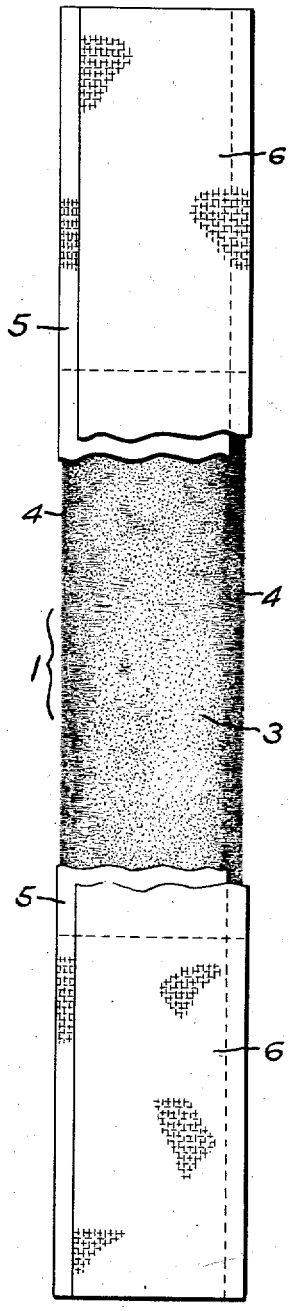
Fig. 1 is a bottom plan or outer side view of a serviette or sanitary napkin embodying one form of my invention and constructed in accordance with one method thereof.

The superposed webs, now moisture-proofed on one surface, are then divided up into packages or pads of the desired size and shape, substantially as illustrated in Figs. 1 and 2. Preferably said webs are fed beneath or between rotary cutting devices which desirably are provided with serrated edges and which sever the material with a sawing rather than a pressure-cutting or pinching action. In said manner the fibres are not matted or compacted at the severed edges but are actually separated or frayed, as indicated at 4 in Figs. 1 and 3.

Suitable means for supporting or attaching the absorbent pad thus formed is then provided, herein comprising a covering or envelope of gauze 5 wrapped about the pad without fastening thereto and extending longitudinally beyond the same at opposite ends, affording attaching flaps 6, 6. Said covering as well as the pad itself, is desirably free of stitching or other securing means so that it may easily be removed after use of the napkin and disposed of separately but permissibly in the same manner as the readily disintegrated absorbent element itself.

In certain of the claims I have defined the part made up of the layers 2 as forming a pad portion, and have referred to said pad portion with the additional part 3, as together constituting the pad. It will be noted that the pad portion is readily disintegrable so that the pad almost in its entirety is disintegrable and the entire pad is capable of similar disposal after use.

While for the purpose of illustration I have referred to film-like strips or webs of cellulosic material forming the main portion of the pad, which film-like strips I deem preferable, it will be understood that within the scope of my invention a plurality of layers, sheets, or webs of like cellulosic material of a greater or less thickness may be employed so long as the desired characteristics of softness, flexibility, ability to disintegrate and the others above mentioned are retained.

My invention is not limited to the specific form or method herein shown and described, the scope thereof being pointed out in the following claims.

Claims.

1. In a sanitary napkin, a multiplicity of superposed, thin webs of wood cellulose forming a pad portion which is readily disintegrable after use, and an additional soft, flexible thin sheet of substantially similar material suitably moisture-proofed and laid upon said pad portion without positive attachment thereto, affording no obstruction to the disintegration of the said pad portion, and being itself capable of disposal in the same manner as the said pad portion, whereby a moisture proofed flexible and non-irritating pad readily disintegrable almost in its entirety, and all capable of similar disposal after use, is provided.

2. In a sanitary napkin, a multiplicity of superposed, thin webs of wood cellulose, constituting a pad portion and an additional thin sheet of similar wood cellulose of a closer texture than that of said films, suitably moisture-proofed and laid upon said pad portion without positive attachment thereto, the edges of said cellulose sheets being frayed and uncompacted in the formation of said pad portion to avoid all possibility of irritation thereby to the user.

3. A sanitary napkin comprising a plurality of tenuous webs of ligno-cellulose material in superposed relation forming a soft, highly flexible absorbent pad portion readily disintegrable when discarded after use, an envelope of gauze surrounding said flexible pad portion and retaining the said plurality of webs in said superposed relation and extending longitudinally beyond the latter at their opposite ends to provide securing means for the napkin, and a thin layer of material similar in character to that of said pad portion suitably moisture proofed and constituting moisture-retaining means at the outer face of said pad portion intermediate the latter and said gauze envelope and held in position thereby, said moisture-retaining means having substantially the same degree of flexibility and softness as that of the said pad portion, whereby the softness and flexibility of the latter are preserved, and being free of positive attachment to the pad portion thereby presenting no obstruction to the ready disintegration of the latter when freed from its gauze envelope for discarding after use, said means being itself capable of disposal in the same manner as the said pad portion and envelope.

4. That method of making an absorbent pad particularly adapted for hygienic and surgical purposes which consists in superposing a multiplicity of film-like sheets of wood cellulose of relative large area, in applying moisture-proofing material to a sheet of similar but desirably less tenuous wood cellulose, in laying said moisture-proofed sheet when drained but moist upon said multiplicity of sheets whereby the moisture proofing material is prevented from permeating more than one or a small plurality of the adjacent sheets, and in dividing said sheets transversely into pads of the desired size.

5. That method of making an absorbent pad particularly adapted for hygienic and surgical purposes which consists in superposing a multiplicity of film-like sheets of wood cellulose of relative large area, in applying moisture-proofing material to a sheet of similar but desirably less tenuous wood cellulose. in laying said moisture proofed sheet when drained but moist upon said multiplicity of sheets whereby the moisture proofing material is prevented from permeating more than one or a small plurality of the adjacent sheets and in dividing said sheets transversely into pads of the desired size by a saw-cutting action whereby the edges of said pads are prevented from matting.

6. A sanitary napkin comprising in combination an absorbent pad portion formed of a plurality of soft, highly flexible, superposed ligno-cellulose webs, whereby said pad portion is disposable after use by depositing it in and flushing a usual water-containing toilet vault and is readily disintegrable in the water thereof or flowing therefrom, an envelope of gauze surrounding said flexible pad portion and retaining said plurality of webs in said superposed relation and extending longitudinally beyond the latter at their opposite ends to provide securing means for the napkin, and a soft, highly flexible, thin, moisture-proof sheet constituting moisture-retaining means at the outer face of said pad portion intermediate the latter and said gauze envelope, said moisture-retaining means having substantially the same degree of flexibility and softness as that of said pad portion, whereby the softness and flexibility of the latter are preserved, said moisture-proof sheet extending over at least the major central region of the adjacent face of the pad portion but leaving the longitudinal side edges of the latter substantially wholly exposed to the action of the water when deposited therein with said sheet, presenting no obstruction to the ready disintegration of said pad portion when freed from its gauze envelope for discarding after use, and being itself capable of disposal through the same toilet facilities above mentioned.

7. A sanitary napkin comprising a soft, flexible, absorbent pad portion formed of a plurality of ligno-cellulose layers whereby it is disposable after use by depositing it in and flushing a usual water-containing toilet vault and is readily disintegrable in the water thereof or flowing therefrom, an envelope of gauze surrounding said pad portion and extending longitudinally beyond the same at its opposite ends to provide securing means for the napkin, and a soft, highly flexible, thin, moisture-proof sheet at one outer face of said pad portion and within said gauze envelope, said moisture-proof sheet having substantially the same degree of flexibility and softness as that of said pad portion, whereby the flexibility and softness of the latter are preserved, and presenting no obstruction to the ready disintegration of the pad portion, said moisture-proof sheet being itself capable of disposal through the same toilet facilities above mentioned, the edges of said layers forming the pad portion being frayed and uncompacted to reduce possibility of irritation thereby to the user.

8. In a sanitary napkin, a plurality of superposed sheets of wood cellulose constituting a pad portion, and a soft, highly flexible, moisture-proof sheet providing moisture-retaining means at one face of said pad portion, the edges of said cellulose sheets being frayed and uncompacted in the formation of said pad portion to reduce possibility of irritation thereby to the user.

In testimony whereof, I have signed my name to this specification.

ERROLD B. THOMAS.